US00PP07782P

United States Patent [19]

DeCoster

[11] Patent Number: Plant 7,782

[45] Date of Patent: Feb. 4, 1992

[54] PHILODENDRON PLANT NAMED SPLENDOR

[76] Inventor: Paul DeCoster, Brusselsesteenweg 94, 9230 Melle, Belgium

[21] Appl. No.: 556,538

[22] Filed: Jul. 23, 1990

[51] Int. Cl.[5] ..... A01H 5/00

[52] U.S. Cl. ..... Plt./88

[58] Field of Search ..... Plt./88

*Primary Examiner*—James R. Feyrer

*Attorney, Agent, or Firm*—Foley & Lardner

[57] ABSTRACT

A new philodendron plant named Splendor, characterized by its rigid petioles and erect leaves, excellent leaf retention with no changes in color, relatively short internodes for a vertically grown cultivar, slow and vigorous growth, and its ability to be efficiently propagated by tissue culture.

3 Drawing Sheets

BACKGROUND OF THE INVENTION

The present invention comprises a new and distinct cultivar of philodendron plant named Splendor.

The new cultivar was discovered growing among several hundred random seedlings obtained in approximately September of 1977 from Bamboo Nursery, Opapka, Fla. The plants were approximately 3–4" long with roots, but not rooted in soil, and were indistinguishable one from the other at the time of purchase. The parentage of the new cultivar was not known at the time of acquisition, nor is it now known.

When the seedlings were grown to mature plants by the applicant in Melle, Belgium in the greenhouses of the applicant, the novel characteristics of the new cultivar were readily evident. Asexual reproduction by me of the new cultivar by tissue culture beginning in approximately 1986 in Melle, Belgium, and repeated asexual reproduction thereafter, has demonstrated that Splendor retains its distinctive characteristics through successive propagation.

The following characteristics in combination distinguish Splendor from other philodendron cultivars of this general type.

1. Vertical growth habit, with the plant normally being attached to a moss pole or similar support to better express its vertical growth.
2. Relatively short internodes for a vertically grown cultivar, thereby producing an abundance of foliage.
3. Slow and vigorous growth, resulting in a strong plant.
4. Propagates very efficiently by tissue culture.
5. Strong and resistant.
6. Slower grower than Red Emerald.
7. Does not lose its older leaves, which remain perfect in color and shape.

Sheet 1 is a perspective photographic drawing of the plant Splendor taken when the plant was approximately 18 months old and in flower.

Sheet 2 is a photographic drawing taken under the same conditions as sheet 1, showing in more detail the leaf and petiole characteristics of Splendor.

Sheet 3 is a photographic drawing showing more clearly the size and shape of a typical leaf of the plant taken under the conditions described in connection with Sheet 1.

The following observations and measurements are based on plants of Splendor 18 months in age grown in 40 cm pots in Melle, Belgium in greenhouses in accordance with standard commercial practices. Color values are based on The Royal Horticultural Society Colour Chart (R.H.S.). The color values were measured in May 1990 at approximately 3 p.m. under natural light conditions.

FORM CHARACTERISTICS

Leaf:

*Shape.*—Mature: Generally ovate, tapering to a pointed tip, the bottom of the leaf being concavely shaped at the petiole, and undulating or wavy in the direction of length, particularly at the edge. Immature: Generally ovate or elliptical, with the bottom of the leaf at the petiole being narrowly indented. Tip: Cuspidate. Base: Auriculate. Margin: Smooth; narrow but visible (less than 1 mm) red band about the entire edge. Venation: Visible, light-green veins on top of leaf; bright red to purplish red veins on bottom of leaf.

*Arrangement.*—Alternate.

*Attachment.*—Stalked.

Petiole: Rigid, extending into the concave portion of the leaf, flat on upper top surface.

APPROXIMATE SIZE CHARACTERISTICS OF TYPICAL COMMERCIAL PLANT

Leaf:

*Width at widest point.*—24 cm.

*Width 1" from top.*—4.5 cm.

*Length.*—45 cm.

Petiole:

*Length.*—33 cm.

*Diameter (center).*—1.2 cm.

Internode spacing: Approximately 5–6 cm.

Overall plant height at 18 months: 2 m.

COLOR CHARACTERISTICS

Leaf:

*Mature.*—Upper surface, closest to 137A but somewhat darker; purple 183A margin all around; under surface, base color is green (closest to 146B) to greyed green (closest to 197A) heavily infused with greyed purple 187B to give general appearance of reddish green in determinant color value.

*Immature.*—When just opening or unfurling, purplish-green changing to yellow-green 148, then gradually darkening to 137A and darker when fully opened; underside, when just opening is greyed-red 182, becoming 182B infused with green, changing to an almost reddish brown (176B-C is not precise but is represented as base color), then changing to gray-brown-green (base color is closest to 197A but more brown) infused with red venation, and finally to mature reddish-green color of indeterminant value.

*Venation.*—Very pronounced and extending midrib to margin; on leaves just opening and immature, venation is 185A-B; venation gradually darkens during maturation to approximately 187B; main lateral veins and smaller veins between such lateral veins tend to heavily infuse underside of leaf to give distinctly reddish tone at all stages of maturation.

*Petiole.*—When leaf just opening, color approximately 59-AB, maturing to 187A-B when leaf is fully opened; surface is relatively shiny when just unsheathed, becoming dull on maturity.

Flower:

*Outside of flower.*—59A.

*Inside of flower.*—61B.

Bract: 59A.

OTHER FEATURES

Bud sheaths: Approximately 25–28 cm long and, when opening or unfurling, approximately 59A-B on outside and slightly lighter 59B-C on inside; sheath gradually darkens to a red-purple deeper than 59A, and the sheath gradually deteriorates.

Aerial roots: Produced at every leaf joint; normally 3 roots at approximately same level extend from periphery of stalk at circumferencely spaced positions; roots are fibrous and encased in covering layer which eventually deteriorates; the aerial roots when fresh are red-purple and turn to brown during maturation. The roots are typically 4–5 millimeters in diameter and approximately double the diameter of the aerial roots of the cultivar Red Emerald. Both cultivars tend to produce aerial roots in substantial quantity.

I claim:

1. A new and distinct philodendron plant named Splendor, as described and illustrated.

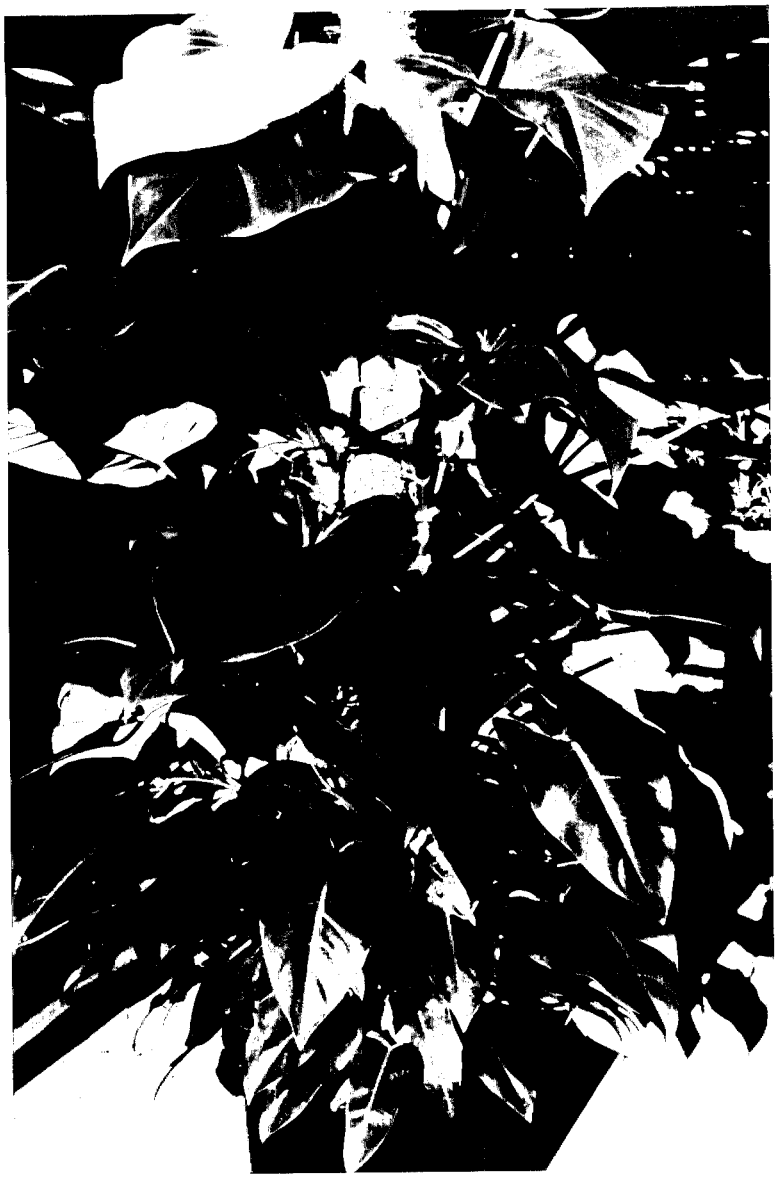

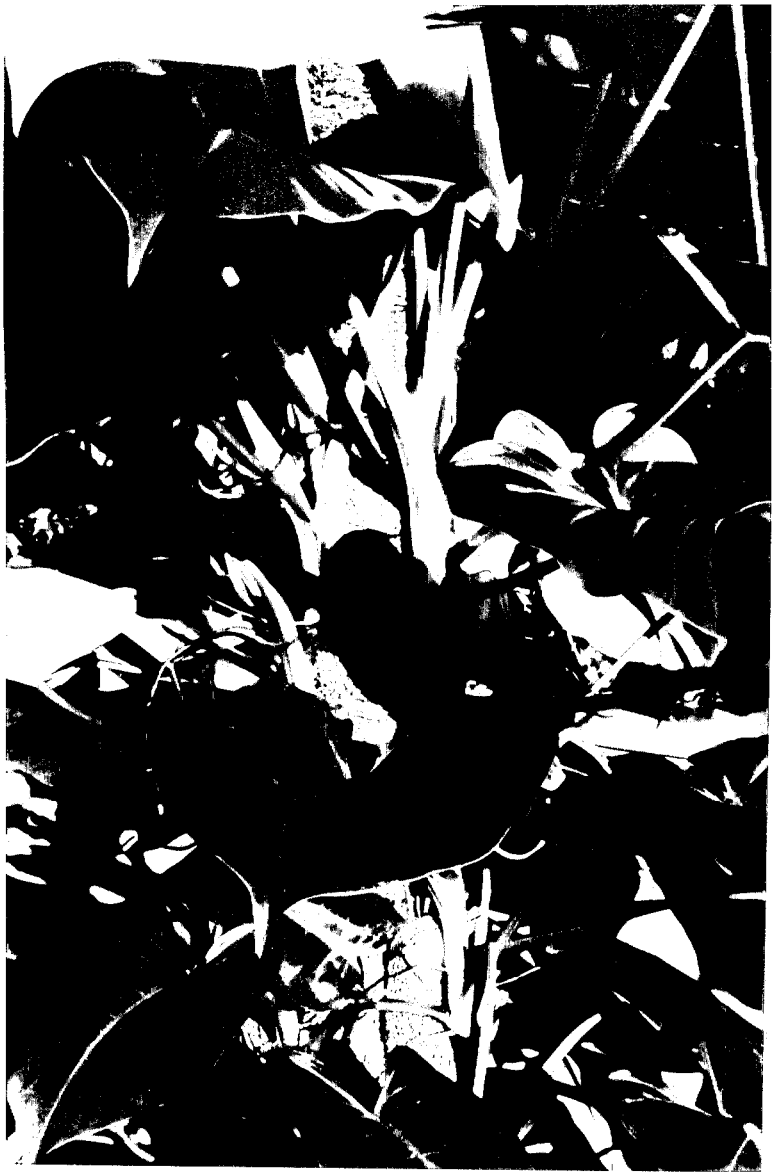

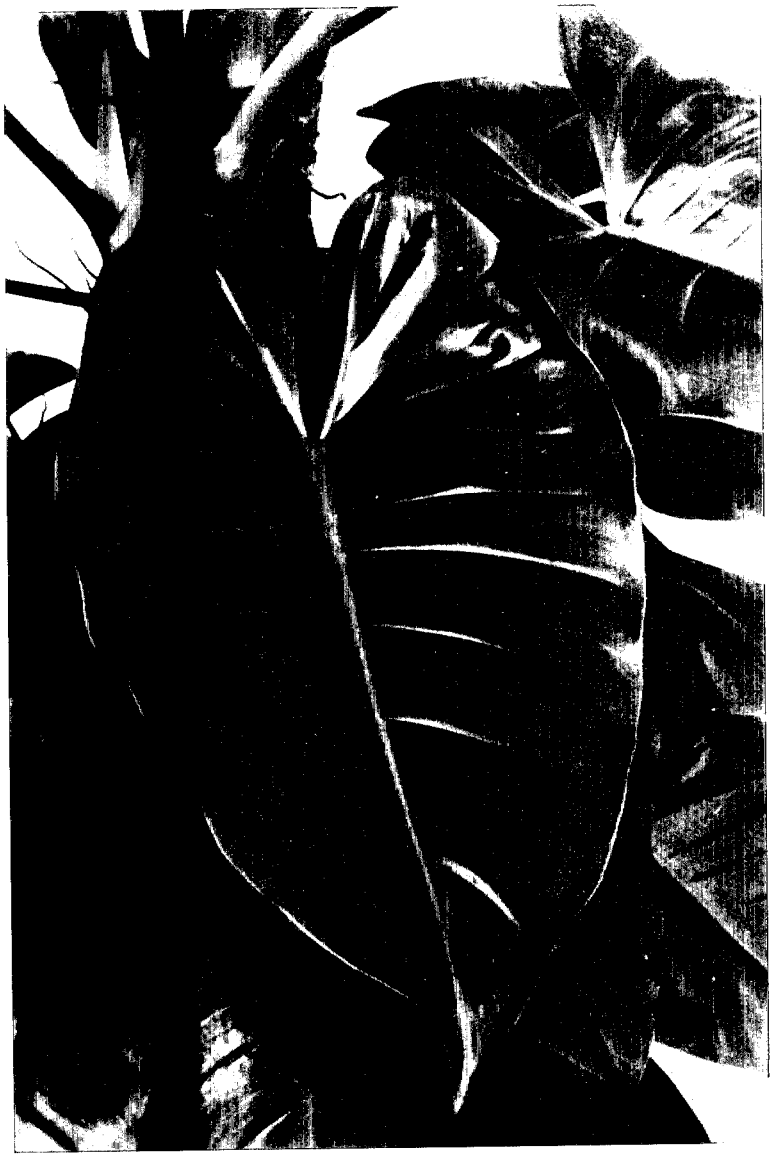

* * * * *